United States Patent
Klopp et al.

(10) Patent No.: US 6,965,047 B2
(45) Date of Patent: Nov. 15, 2005

(54) METHOD FOR PRODUCING ETHERS, ESTERS OR ACID ANHYDRIDES

(75) Inventors: Ingo Klopp, Weisenheim (DE); Thomas Bogenstätter, Bad Dürkheim (DE); Dirk Franke, Birkenheide (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/511,161

(22) PCT Filed: Apr. 14, 2003

(86) PCT No.: PCT/EP03/03867

§ 371 (c)(1),
(2), (4) Date: Oct. 14, 2004

(87) PCT Pub. No.: WO03/087025

PCT Pub. Date: Oct. 23, 2003

(65) Prior Publication Data

US 2005/0165248 A1    Jul. 28, 2005

(30) Foreign Application Priority Data

Apr. 15, 2002 (DE) ............................ 102 16 638

(51) Int. Cl.$^7$ .................................................. C07C 69/76
(52) U.S. Cl. ................................................... 560/107
(58) Field of Search ........................................ 560/107

(56) References Cited

U.S. PATENT DOCUMENTS 6,818,793 B2 * 11/2004 Wulff et al. .................. 562/18

FOREIGN PATENT DOCUMENTS

| DE | A 3 129 379 | 2/1983 |
| EP | 1 240 173 B1 | 5/2003 |
| WO | WO03/020411 A1 | 3/2003 |

OTHER PUBLICATIONS

Bollmacher et al., Chemiker—Zeitung 107 (1983), No. 4, pp. 121-126.

* cited by examiner

Primary Examiner—Paul A. Zucker
(74) Attorney, Agent, or Firm—Novak Druce & Quigg, LLP; Jason D. Voight

(57) ABSTRACT

Ethers, esters or acid anhydrides are advantageously obtained when a cake of a first reactant selected from salts of organic or oxygen-containing inorganic acids or alkoxides disposed on a filter element is flowed through by a solution of a second reactant selected from inorganic or organic acid halides and alkyl halides, so that the insoluble halide salt formed remains on the filter element. The halide salt can thus be removed substantially quantitatively in a simple manner.

5 Claims, No Drawings

METHOD FOR PRODUCING ETHERS, ESTERS OR ACID ANHYDRIDES

The present invention relates to a process for preparing ethers, esters or acid anhydrides, in which a first reactant selected from salts of organic or oxygen-containing inorganic acids and alkoxides is reacted with a second reactant selected from inorganic or organic acid halides and alkyl halides. The esters may be those of organic or inorganic acids, and the acid anhydrides those of organic acids, in particular carboxylic anhydrides, or mixed anhydrides of organic and oxygen-containing inorganic acids.

An example of such a process is the preparation of ethers or esters by the Williamson synthesis or the preparation of mixed acid anhydrides by reaction of a salt of a first acid with the halide of a second acid. The halide salt formed as a coupling product in these syntheses is insoluble in many organic solvents.

An industrially significant example is the reaction of sodium benzoate or ammonium benzoate with phosphorus (III) chloride to give tribenzoyl phosphite and sodium chloride or ammonium chloride. The tribenzoyl phosphite can then be reacted with triscyanomethylhexahydrotriazine and the reaction product hydrolyzed to N-phosphonomethylglycine which is known under the name glyphosate and is a total herbicide used on a large scale. For the further reaction of tribenzoyl phosphite mentioned, the preceding complete removal of the sodium chloride or ammonium chloride formed is advantageous.

Bollmacher, H. and Satori, P. describe the preparation of tribenzoyl phosphite in Chemiker-Zeitung 107 (1983) No. 4, p. 121–126. Sodium benzoate is suspended in anhydrous ether and admixed with phosphorus(III) chloride. The solvent is then distilled off under high vacuum and by-products formed are removed by treating heating with hexane.

It is possible to remove the insoluble halide salt from the solution of the desired ether, ester or acid halide by filtration. However, the filtration presents problems, particularly on the industrial scale. In reactions of the type described in which one reactant is an insoluble solid while the other reactant is dissolved in a liquid phase, the chemical reaction takes place on the surface or in the immediate vicinity of the surface of the solid reactant. The insoluble reaction product forms on the surface of the solid reactant. The contact points between the initially charged solid reactant and the forming insoluble reaction product are extremely fragile. Also, the volume of the solid reactant in the course of the reaction reduces constantly, so that at the end of the reaction there is only a loose agglomerate of the insoluble reaction product. In many cases, the reaction product forming on the surface of the solid reactant forms porous structures which have a low mechanical stability. Even small mechanical stresses are sufficient to free the insoluble reaction product from the surface of the solid reactant, and to destroy the loose agglomerate of the insoluble reaction product. Intensive stirring in the reaction leads to the formation of very fine solids which are therefore difficult to filter. The greater the batchsize chosen, the more marked these disadvantages are, since the greater shear at the stirrer in large batches has the consequence of increasing the attrition.

It is an object of the present invention to provide a process as specified at the outset by which the insoluble halide salt can be removed substantially quantitatively in a simple manner.

DE-A 31 29 379 discloses a procedure for further reaction of a precipitated dye or dye intermediate. The precursor is filtered off and washed; the conversion to the end product is effected without an intermediate stage in the fixed bed of the precursor formed in the filtration. The document is concerned exclusively with dyes and dye intermediates. No reference is made to problems with the filterability of the insoluble reaction product formed.

We have found that the object is achieved by a process in which a cake of the first reactant disposed on a filter element is flowed through by a solution of the second reactant, so that the insoluble halide salt formed remains on the filter element.

In the process according to the invention, the halide salt formed in the reaction remains on the filter element and is therefore subjected to no shear forces by stirrers, pumps and the like. The formation of fine particles is strongly suppressed. The desired ether, ester or acid anhydride is obtained as a filtrate in the form of a solution from which the ether, ester or the acid anhydride can be isolated if desired. However, preference is given to using the solution as such in further reactions.

The solvent in which the second reactant is dissolved is chosen in such a manner that it is inert toward the reactants used and the reaction products, and the halide salt formed in the reaction is insoluble in it. For the purposes of the present invention, "insoluble" means a solubility of less than 1 g/100 ml at the reaction temperature.

Examples of useful filter elements include belt filters, rotary filters, filter presses, or preferably suction, pressure or vacuum filters, or else plate or disk filters.

The way in which the cake of the first reactant is flowed through by the solution of the second reactant is subject to no restrictions. For instance, the solution may be applied to the cake in surges or continuously and be allowed to run through by the action of gravity, be forced through the cake by means of pressure or be sucked through by applying a vacuum on the opposite side of the filter element. Advantageously, the application is effected in such a manner that a liquid column forms above the cake in order to achieve a uniform penetration of the cake. Alternatively, the cake can be flooded from below through the filter element with the solution, and the solution can then be sucked through the filter element again, and this procedure is preferably repeated once or more than once.

The reaction temperature is chosen depending on the reactivity of the reactants and advantageously in such a manner that the second reactant and the reaction product are sufficiently soluble in the solvent; the upper limit of the reaction temperature is the boiling point of the solvent. The reaction temperature is generally less than 100° C. and is preferably from 0 to 50° C.

Useful salts of organic or oxygen-containing inorganic acids are the alkali metal, alkaline earth metal or ammonium salts of aliphatic, aromatic or heteroaromatic carboxylic acids or sulfonic acids. These include $C_1$–$C_{18}$-alkanecarboxylic acids such as formic acid, acetic acid or propionic acid, and also mono- or bicyclic aromatic carboxylic acids which optionally have one or two ring heteroatoms selected from nitrogen, oxygen and sulfur, and may bear from one to four substituents selected independently from $C_1$–$C_4$-alkyl, $C_1$–$C_4$-alkoxy, nitro and halogen, such as benzoic acid, naphthoic acid or pyridinecarboxylic acid.

Useful alkoxides are the alkali metal or alkaline earth metal salts of alcohols or phenols. These include straight-chain or branched $C_1$–$C_{18}$-alkanols such as methanol or ethanol, and also mono- or bicyclic aromatic hydroxyl compounds which may be substituted as above.

Among the alkali metal salts, preference is generally given to the sodium and potassium salts. Particular preference is also given to the ammonium salts which may be derived from ammonia and amines. Examples of these include tetra-$C_1$–$C_{18}$-alkylammonium salts in which the alkyl radicals may be the same or different. Salts having unsubstituted ammonium ions are particularly suitable.

Useful inorganic acid halides are in particular chlorides, for example phosphorus(III) chloride, phosphorus(V) chloride, thionyl chloride or sulfuryl chloride. Useful organic acid chlorides include aliphatic, aromatic or heteroaromatic acid halides, in particular the chlorides. These include the halides of $C_1$–$C_{18}$-alkanecarboxylic and sulfonic acids such as acetyl chloride, propionyl chloride or methanesulfonyl chloride, and also the halides of mono- or bicyclic aromatic carboxylic acids or sulfonic acids which may be substituted as above, such as benzoyl chloride, benzenesulfonyl chloride or p-toluenesulfonyl chloride.

Useful alkyl halides are primary, secondary or tertiary alkyl chlorides, bromides or iodides. These include straight-chain or branched $C_1$–$C_{18}$-alkyl halides such as methyl chloride, ethyl chloride or tert-butyl chloride.

Useful solvents include aliphatic and aromatic hydrocarbons such as hexane, heptane, octane, isooctane, cyclohexane, methylcyclohexane, benzene, alkylbenzenes having up to three $C_1$–$C_4$-alkyl radicals on the aromatic ring such as toluene, o-, m- and p-xylene and their mixtures; halogenated hydrocarbons, in particular chlorinated hydrocarbons, such as dichloromethane, trichloromethane, 1,2-dichloroethane, 1,1,2-trichloroethane, chlorobenzene, perchloroethylene, 1,2-dichloropropane; fluorinated hydrocarbons such as fluorobenzene or fluoroalkyl-substituted benzenes; ethers such as diethyl ether, diisopropyl ether, dioxane, tetrahydrofuran, dimethoxyethane, diethylene glycol dimethyl ether; ketones such as acetone, cyclohexanone, methyl isobutyl ketone; or esters such as ethyl acetate; organic nitro compounds such as nitromethane or nitrobenzene.

The solvent is preferably used in substantially anhydrous form, i.e. the water content of the suspension medium is preferably less than 0.5% by weight, in particular less than 0.1% by weight.

The process according to the invention has proven particularly useful for preparing tribenzoyl phosphite by using alkali metal salt or the ammonium salt of benzoic acid as the first reactant, and phosphorus(III) chloride as the second reactant. A useful solvent for this reaction is 1,2-dichloroethane.

Advantageously, the cake of the first reactant is obtained by precipitating the first reactant out of a reaction solution and filtering the suspension obtained through the filter element, and optionally washing it once or more than once, for example by flowing through, with a suitable washing liquid. For example, ammonium benzoate can be precipitated by treating a solution of benzoic acid in, for example, 1,2-dichloroethane with gaseous ammonia. The ammonium benzoate suspension is filtered through the filter element and the ammonium benzoate filter cake, according to the invention, is then flowed through by a solution of the second reactant, for example a solution of phosphorus(III) chloride in 1,2-dichloroethane.

The invention is illustrated by the examples which follow.

EXAMPLES

Example 1

A glass pressure tube having a frit of length about 50 cm and diameter 5.0 cm was charged with 389 g (2.80 mol) of ammonium benzoate (Fluka) to a height of 31 cm. 1423 g of 1,2-dichloroethane (DCE) were pumped in circulation through the fixed ammonium benzoate bed from a reservoir connected to the pressure tube. The flow through the fixed bed was 350 ml min$^{-1}$ at a pressure drop of 80 mbar. The liquid volume of the tubes and fixed bed was 300 ml. 124.2 g (0.90 mol) of PCl$_3$ were added dropwise to the reservoir within 30 minutes. The feed to the pressurized tube was cooled to about 10° C., so that the temperatures in the tube did not exceed 30 to 35° C. After the end of the PCl$_3$ addition, circulation was continued for a further 30 minutes. Analysis: benzoic acid content in the filtrate 18.6%; filter resistance of the ammonium benzoate at the beginning of the reaction $1.1*10^{10}$ mPa.s.m$^{-2}$; filter resistance of the ammonium chloride after the end of the reaction $5.0*10^{10}$ mPa.s.m$^{-2}$.

Example 2

In a glass pressure tube having a frit of length about 10 cm and diameter 5.0 cm, 25.8 g (0.19 mol) of ammonium benzoate prepared by reacting a solution of benzoic acid in DCE with gaseous NH$_3$ were filtered. 406 g of 1,2-dichloroethane (DCE) were pumped in circulation through the fixed ammonium benzoate bed from a reservoir connected to the pressure tube. The flow through the fixed bed was 50 ml min$^{-1}$. 8.2 g (0.06 mol) of PCl$_3$ were added dropwise to the reservoir within 20 minutes. The temperature of the solution was maintained between 25 and 30° C. After the end of the PCl$_3$ addition, circulation was continued for a further 38 minutes. Analysis: benzoic acid content in the filtrate 3.11%; filter resistance of the ammonium chloride after the end of the reaction $2.2*10^{13}$ mPa.s.m$^{-2}$.

Example 3

A glass pressure tube having a frit of length about 10 cm and diameter 5.0 cm was charged with 56.0 g (0.40 mol) of ammonium benzoate (Fluka) to a height of 5.5 cm. 406 g of 1,2-dichloroethane (DCE) were pumped in circulation through the fixed ammonium benzoate bed from a reservoir connected to the pressure tube. The flow through the fixed bed was 170 ml min$^{-1}$. 17.8 g (0.13 mol) of PCl$_3$ were added dropwise to the reservoir within 10 minutes. The temperature of the solution was maintained between 25 and 30° C. After the end of the PCl$_3$ addition, circulation was continued for a further 30 minutes. Analysis: benzoic acid content in the filtrate 10.04%; filter resistance of the ammonium chloride after the end of the reaction $3.0*10^{11}$ mPa.s.m$^{-2}$.

We claim:

1. A process for preparing ethers, esters or acid anhydrides, in which a cake of a first reactant selected from salts of organic or oxygen-containing inorganic acids or alkoxides disposed on a filter element is flowed through by a solution of a second reactant selected from inorganic or organic acid halides and alkyl halides, so that the insoluble halide salt formed remains on the filter element.

2. A process as claimed in claim 1, in which the second reactant is dissolved in a solvent selected from hydrocarbons, halogenated hydrocarbons, ethers ketones and esters.

3. A process as claimed in claim 2, in which the solvent is selected from 1,2-dichloroethane, 1,2-dichloropropane and mixtures thereof.

4. A process as claimed in claim 1, in which the first reactant used is an alkali metal salt or the ammonium salt of benzoic acid and the second reactant used is phosphorus(III) chloride.

5. A process as claimed in claim 1 in which the cake of the first reactant is obtained by precipitating the first reactant out of a reaction solution and filtering the suspension obtained through the filter element.

* * * * *